(12) United States Patent
Liu (10) Patent No.: US 11,097,427 B2
(45) Date of Patent: Aug. 24, 2021

(54) HANDHELD DEVICE AND HAND TREMOR COMPENSATION METHOD

(71) Applicant: BOE TECHNOLOGY GROUP CO., LTD., Beijing (CN)

(72) Inventor: Cheng Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 552 days.

(21) Appl. No.: 15/989,222

(22) Filed: May 25, 2018

(65) Prior Publication Data

US 2019/0022871 A1 Jan. 24, 2019

(30) Foreign Application Priority Data

Jul. 20, 2017 (CN) .......................... 201710597717.2

(51) Int. Cl.
*B25J 13/08* (2006.01)
*A61B 5/11* (2006.01)
(Continued)

(52) U.S. Cl.
CPC ........... *B25J 13/088* (2013.01); *A61B 5/1101* (2013.01); *A61B 5/1121* (2013.01);
(Continued)

(58) Field of Classification Search
None
See application file for complete search history.

(56) References Cited

U.S. PATENT DOCUMENTS

| 4,819,843 A | * | 4/1989 | Nakayama | B60N 3/103 108/44 |
| 5,489,055 A | * | 2/1996 | Levy | B60N 3/103 224/544 |

(Continued)

FOREIGN PATENT DOCUMENTS

| CN | 101291120 A | 10/2008 |
| CN | 101612735 A | 12/2009 |

(Continued)

OTHER PUBLICATIONS

First Office Action for Chinese Application No. 201710597717.2, dated Apr. 23, 2019, 11 Pages.

*Primary Examiner* — Jason M Sims
*Assistant Examiner* — James Stewart Stambaugh, III
(74) *Attorney, Agent, or Firm* — Brooks Kushman P.C.

(57) ABSTRACT

A handheld device is provided. The handheld device includes: a functional body to be used by a user; a handle provided with a first detection circuit configured to detect a movement state of the handle to acquire hand tremor information about a hand of the user; a movable connector through which the functional body is movably connected to the handle in such a manner that the functional body is capable of moving relative to the handle; a movement mechanism connected to the functional body and configured to drive the functional body to move relative to the handle; and a control circuit configured to control an operating state of the movement mechanism in accordance with the hand tremor information acquired by the first detection circuit, to drive the functional body to perform compensating movement relative to the handle, thereby to maintain the functional body at a selected position.

9 Claims, 3 Drawing Sheets

(51) Int. Cl.
  *B25J 11/00* (2006.01)
  *G05B 19/404* (2006.01)
  *A61B 5/00* (2006.01)
  *A47G 19/22* (2006.01)

(52) U.S. Cl.
  CPC ........... *A61B 5/6887* (2013.01); *B25J 11/009* (2013.01); *G05B 19/404* (2013.01); *A47G 19/22* (2013.01); *A47G 2200/046* (2013.01); *A61B 2560/0431* (2013.01); *G05B 2219/41116* (2013.01)

(56) References Cited

U.S. PATENT DOCUMENTS

| | | | |
|---|---|---|---|
| 9,615,683 B2* | 4/2017 | Peacock | A47G 19/2266 |
| 2003/0236475 A1* | 12/2003 | Kalvert | A63B 21/00069 |
| | | | 601/5 |
| 2008/0240704 A1 | 10/2008 | Takahashi | |
| 2010/0228362 A1* | 9/2010 | Pathak | A61F 4/00 |
| | | | 623/65 |
| 2011/0013030 A1 | 1/2011 | Lee | |
| 2014/0052275 A1* | 2/2014 | Pathak | A47G 21/08 |
| | | | 623/65 |
| 2014/0125824 A1 | 5/2014 | Takizawa | |
| 2017/0100272 A1* | 4/2017 | Pathak | A61J 7/00 |

FOREIGN PATENT DOCUMENTS

| | | |
|---|---|---|
| CN | 201528931 U | 7/2010 |
| CN | 101957536 A | 1/2011 |
| CN | 103605250 A | 2/2014 |
| CN | 103649828 A | 3/2014 |
| CN | 103906483 A | 7/2014 |
| CN | 104586176 A | 5/2015 |
| CN | 106108564 A | 11/2016 |
| EP | 2645905 B1 | 12/2016 |
| WO | 2015003133 A1 | 1/2015 |

\* cited by examiner

Fig. 5

HANDHELD DEVICE AND HAND TREMOR COMPENSATION METHOD

CROSS-REFERENCE TO RELATED APPLICATION

This application claims priority to Chinese Patent Application No. 201710597717.2 filed on Jul. 20, 2017, which is incorporated herein by reference in its entirety.

TECHNICAL FIELD

The present disclosure relates to articles for daily use, in particular to a handheld device and a hand tremor compensation method.

BACKGROUND

For a person with a hand tremor symptom, e.g., a Parkinson's patient or an aged person being weak in hands, it may be difficult to use such articles for daily use as cups. Currently, some specific cups or cup-holding mechanisms have been proposed for persons with the hand tremor symptom, so as to reduce the tremor of the cups.

However, there still exist some problems for these specific cups or cup-holding mechanisms in the related art. For example, for the specific cups or cup-holding mechanism, a mechanical structure for cancelling out the tremor is merely capable of moving within a limited range, so the use thereof is inflexible. For some schemes, it is impossible to differentiate the hand tremor from normal movement. In addition, for a method or device for canceling out the unintentional tremor in the related art, it is merely able to cancel out a translational tremor rather than a rotational tremor.

SUMMARY

In one aspect, the present disclosure provides in some embodiments a handheld device, including: a functional body to be used by a user; a handle capable of being held by a user and provided with a first detection circuit configured to detect a movement state of the handle so as to acquire hand tremor information about the hand of the user holding the handle; a movable connector through which the functional body is movably connected to the handle in such a manner that the functional body is capable of moving relative to the handle; a movement mechanism connected to the functional body and configured to drive the functional body to move relative to the handle; and a control circuit configured to control an operating state of the movement mechanism in accordance with the hand tremor information about the hand of the user acquired by the first detection circuit, so as to drive the functional body to perform compensating movement relative to the handle, thereby to maintain the functional body at a selected position.

In a possible embodiment of the present disclosure, the hand tremor information includes rectilinear movement information about the hand of the user in an X-axis direction, a Y-axis direction and a Z-axis direction in a three-dimensional coordinate system, and rotational angle information about the hand of the user acquired in the case that the hand rotates about at least two coordinate axes in the three-dimensional coordinate system as central axes. The movement mechanism is at least capable of driving the functional body to move rectilinearly relative to the handle in the X-axis direction, the Y-axis direction and the Z-axis direction in the three-dimensional coordinate system, and capable of controlling the functional body to rotate relative to the handle about the at least two coordinate axes in the three-dimensional coordinate system as the central axes. The control circuit is further configured to acquire, in accordance with the hand tremor information about the hand of the user acquired by the first detection circuit, rectilinear movement components of the handle in the X-axis direction, the Y-axis direction and the Z-axis direction in the three-dimensional coordinate system and rotational movement components of the handle in the case that the handle rotates about the at least two coordinate axes in the three-dimensional coordinate system as the central axes, acquire, in accordance with the rectilinear movement components and the rotational movement components, a compensating movement component for cancelling out an influence of the movement of the handle on the movement of the functional body, and control the operating state of the movement mechanism in accordance with the compensating movement component.

In a possible embodiment of the present disclosure, the handle has a main body extending along the Y-axis direction, and a first end and a second end arranged opposite to each other. The first end and the second end of the handle are connected to the functional body through the movable connector.

In a possible embodiment of the present disclosure, the movement mechanism includes a first movement assembly arranged at the first end of the handle and a second movement assembly arranged at the second end of the handle. The first movement assembly includes a first X-axis-direction movement member configured to control the functional body to move rectilinearly relative to the first end of the handle in the X-axis direction, a first Y-axis-direction movement member configured to control the functional body to move rectilinearly relative to the first end of the handle in the Y-axis direction, and a first Z-axis-direction movement member configured to control the functional body to move rectilinearly relative to the first end of the handle in the Z-axis direction. The second movement assembly includes a second X-axis-direction movement member configured to control the functional body to move rectilinearly relative to the second end of the handle in the X-axis direction, a second Y-axis-direction movement member configured to control the functional body to move rectilinearly relative to the second end of the handle in the Y-axis direction, and a second Z-axis-direction movement member configured to control the functional body to move rectilinearly relative to the second end of the handle in the Z-axis direction.

In a possible embodiment of the present disclosure, the control circuit is further configured to, in accordance with the compensating movement component: control the first X-axis-direction movement member and the second X-axis-direction movement member to drive the functional body to move relative to the first end and the second end of the handle in the X-axis direction synchronously, thereby to control the functional body to move rectilinearly in the X-axis direction; control the first X-axis-direction movement member and the second X-axis-direction movement member to drive the functional body to move relative to the first end and the second end of the handle in the X-axis direction asynchronously, thereby to control the functional body to rotate about a Z-axis as the central axis; control the first Y-axis-direction movement member and the second Y-axis-direction movement member to drive the functional body to move relative to the first end and the second end of the handle in the Y-axis direction synchronously, thereby to control the functional body to move rectilinearly in the Y-axis direction; control the first Z-axis-direction movement member and the second Z-axis-direction movement member to drive the functional body to move relative to the first end and the second end of the handle in the Z-axis direction synchronously, thereby to control the functional body to move rectilinearly in the Z-axis direction; and control the first Z-axis-direction movement member and the second Z-axis-direction movement member to drive the functional body to move relative to the first end and the second end of the handle in the Z-axis direction asynchronously, thereby to control the functional body to rotate about an X-axis as the central axis.

In a possible embodiment of the present disclosure, the handle has a main body extending along the Y-axis direction, and a first end and a second end arranged opposite to each other. The first end of the handle is connected to the functional body through the movable connector, and the second end of the handle is not connected to the functional body.

In a possible embodiment of the present discourse, the movement mechanism includes: a third X-axis-direction movement member configured to control the functional body to move rectilinearly relative to the first end of the handle in the X-axis direction; a third Y-axis-direction movement member configured to control the functional body to move rectilinearly relative to the first end of the handle in the Y-axis direction; a third Z-axis-direction movement member configured to control the functional body move rectilinearly relative to the first end of the handle in the Z-axis direction; a first rotation member configured to control the functional body to rotate about an X-axis as the central axis; and a second rotation member configured to control the functional body to rotate about a Z-axis as the central axis.

In a possible embodiment of the present disclosure, the control circuit is further configured to control an operating state of each of the third X-axis-direction movement member, the third Y-axis-direction movement member, the third Z-axis-direction movement member, the first rotation member and the second rotation member in accordance with the compensating movement component.

In a possible embodiment of the present disclosure, the functional body is provided with a second detection circuit configured to detect a movement state of the functional body. The control circuit is further configured to control the operating state of the movement mechanism in accordance with a signal outputted from the second detection circuit, so as to perform negative feedback correction on the compensating movement of the functional body.

In a possible embodiment of the present disclosure, the functional body is further provided with a power source and a charger.

In a possible embodiment of the present disclosure, the handheld device includes a cup, wherein the functional body is a cup body of the cup, and the handle is a cup handle of the cup.

In another aspect, the present disclosure provides in some embodiments a hand tremor compensation method for use in the above-mentioned handheld device, including steps of: detecting a movement state of a handle of the handheld device, so as to acquire hand tremor information about a hand of the user; and driving a functional body of the handheld device to perform compensating movement relative to the handle in accordance with the hand tremor information, so as to maintain the functional body at a selected position.

In a possible embodiment of the present disclosure, the step of detecting the movement state of the handle of the handheld device so as to acquire the hand tremor information about the hand of the user includes: acquiring, in accordance with the acquired hand tremor information about the hand of the user, rectilinear movement components of the handle in an X-axis direction, a Y-axis direction and a Z-axis direction in a three-dimensional coordinate system, and rotational movement components of the handle in the case that the handle rotates about at least two coordinate axes in the three-dimensional coordinate system as central axes.

In a possible embodiment of the present disclosure, the step of driving the functional body of the handheld device to perform the compensating movement relative to the handle in accordance with the hand tremor information about the hand of the user includes: acquiring a compensating movement component for cancelling out an influence of the movement of the handle on the movement of the functional body in accordance with the rectilinear movement components and the rotational movement components, and controlling the compensating movement of the functional body in accordance with the compensating movement component.

In a possible embodiment of the present disclosure, the step of controlling the compensating movement of the functional body in accordance with the compensating movement component includes, in accordance with the compensating movement component: driving the functional body to move relative to a first end and a second end of the handle synchronously in the X-axis direction, so as to control the functional body to move rectilinearly in the X-axis direction; driving the functional body to move relative to the first end and the second end of the handle asynchronously in the X-axis direction, so as to control the functional body to rotate about a Z-axis as a central axis; driving the functional body to move relative to the first end and the second end of the handle synchronously in the Y-axis direction, so as to control the functional body to move rectilinearly in the Y-axis direction; driving the functional body to move relative to the first end and the second end of the handle synchronously in the Z-axis direction, so as to control the functional body to move rectilinearly in the Z-axis direction; and driving the functional body to move relative to the first end and the second end of the handle asynchronously in the Z-axis direction, so as to control the functional body to rotate about an X-axis as a central axis.

In a possible embodiment of the present disclosure, the step of controlling the compensating movement of the functional body in accordance with the compensating movement component includes, in accordance with the compensating movement component, controlling an operating state of each of a third X-axis-direction movement member, a third Y-axis-direction movement member, a third Z-axis-direction movement member, a first rotation member and a second rotation member, so as to control the functional body to move rectilinearly in the X-axis direction, the Y-axis direction and the Z-axis direction, and control the functional body to rotate about a Z-axis and an X-axis as central axes.

BRIEF DESCRIPTION OF THE DRAWINGS

In order to illustrate the technical solutions of the present disclosure in a clearer manner, the drawings desired for the present disclosure will be described hereinafter briefly. Obviously, the following drawings merely relate to some embodiments of the present disclosure, and based on these drawings, a person skilled in the art may obtain the other drawings without any creative effort.

DETAILED DESCRIPTION

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

For a device or method in the related art, it is still impossible to cancel out a hand tremor in a better manner. An object of the present disclosure is to provide a handheld device and a hand tremor compensation method, so as to enable the handheld device to perform corresponding compensating movement in accordance with a hand tremor state of a person, thereby to cancel out the hand tremor and facilitate the use.

Figure 1:
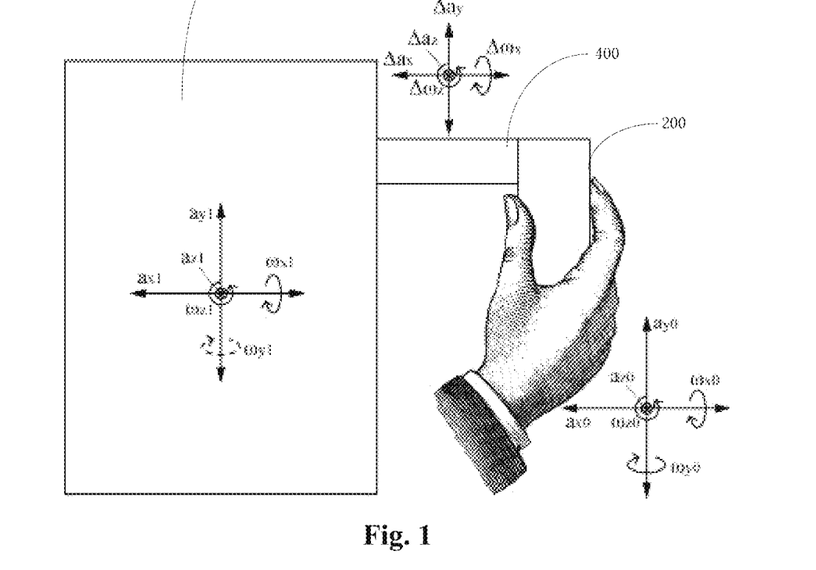
FIG. 1 is a schematic view showing a handheld device according to some embodiments of the present disclosure.
Figure 2:
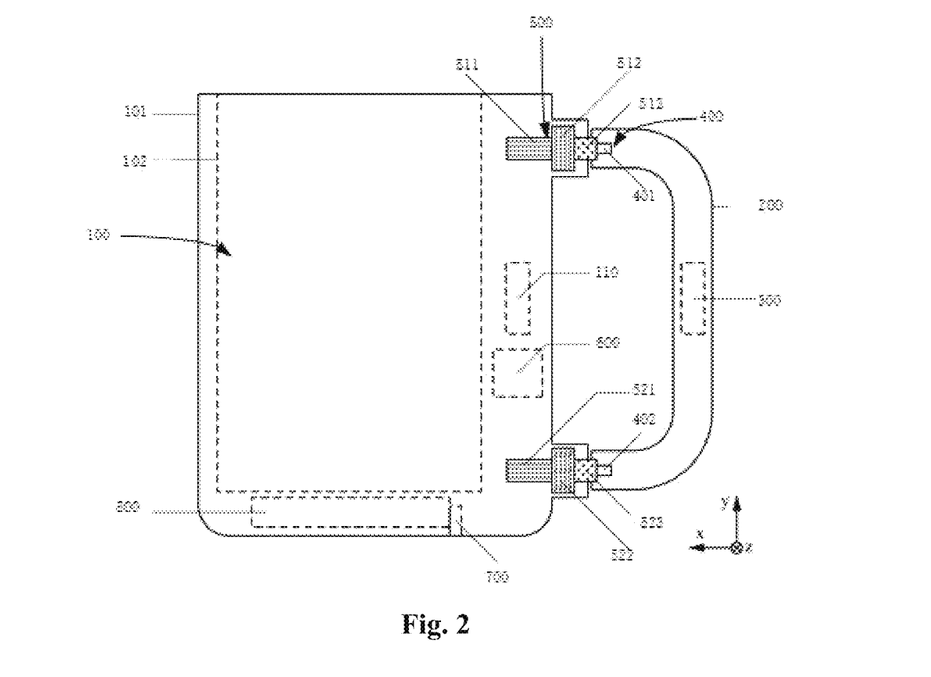
FIG. 2 is another schematic view showing the handheld device according to some embodiments of the present disclosure.
Figure 4:
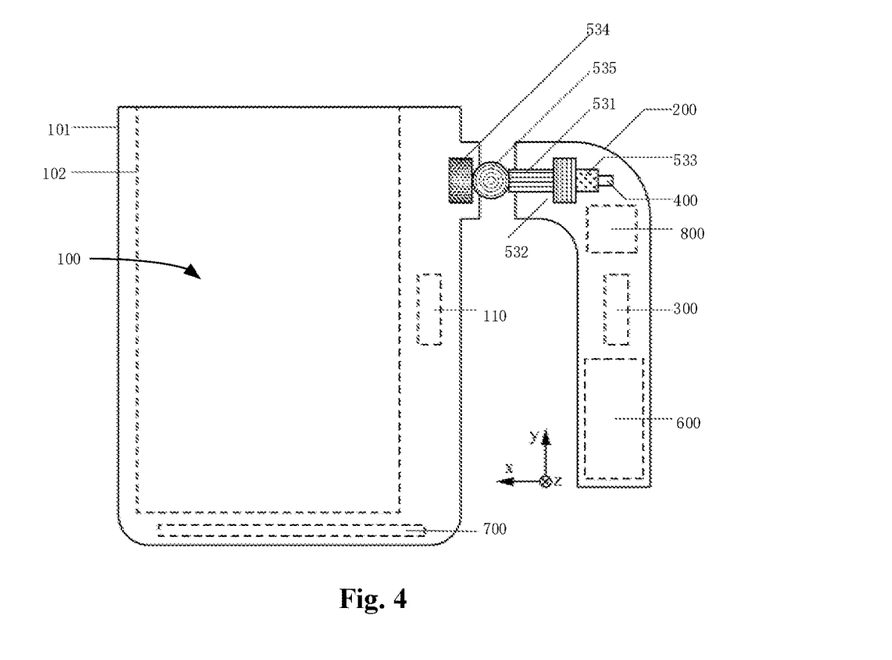
FIG. 4 is a schematic view showing another handheld device according to some embodiments of the present disclosure.

As shown in FIGS. 1, 2 and 4, the present disclosure provides in some embodiments a handheld device, which includes: a functional body 100 to be used by a user and provided with a second detection circuit 110 configured to detect a movement state of the functional body 100; a handle 200 capable of being held by the user and provided with a first detection circuit 300 configured to detect a movement state of the handle 200 so as to acquire hand tremor information about the hand of the user; a movable connector 400 through which the functional body 100 is movably connected to the handle 200 in such a manner that the functional body 100 is capable of moving relative to the handle 200; a movement mechanism 500 connected to the functional body 100 and configured to drive the functional body 100 to move relative to the handle 200; and a control circuit 600 configured to control an operating state of the movement mechanism 500 in accordance with the hand tremor information acquired by the first detection circuit 300, so as to drive the functional body 100 to perform compensating movement relative to the handle 200, thereby to maintain the functional body 100 at a selected position. It should be appreciated that, the selected position may be predetermined in the handheld device, or may be changed along with the movement of the handheld device.

According to the handheld device in the embodiments of the present disclosure, the functional body 100 is movably connected to the handle 200 through the movable connector 400, so that the functional body 100 is capable of moving relative to the handle 200. The movement state of the handle 200 is detected so as to acquire the handle tremor information about the user, and then the functional body 100 is controlled to perform the corresponding compensating movement in accordance with the acquired hand tremor information. As a result, it is able to cancel out the vibration of the functional body 100 caused by the hand tremor of the user, thereby to stabilize the functional body 100 and facilitate the use of the handheld device.

In the embodiments of the present disclosure, the handheld device may be an article for daily use, e.g., cup, bowl, or spoon. The following description will be given by taking the cup as an example. In the case that the handheld device is a cup, the functional body 100 is just a cup body 101 which may be provided with a receiver 102 for receiving a liquid, and the handle 200 is just a cup handle.

In a possible embodiment of the present disclosure, the hand tremor information includes rectilinear movement information about the hand of the user in an X-axis direction, a Y-axis direction and a Z-axis direction in a three-dimensional coordinate system, and rotational angle information about the hand of the user acquired in the case that the hand rotates about at least two coordinate axes in the three-dimensional coordinate system as central axes. The movement mechanism 500 is at least capable of driving the functional body 100 to move rectilinearly relative to the handle 200 in the X-axis direction, the Y-axis direction and the Z-axis direction in the three-dimensional coordinate system, and controlling the functional body 100 to rotate relative to the handle 200 about the at least two coordinate axes in the three-dimensional coordinate system as the central axes. The control circuit 600 is further configured to acquire, in accordance with the hand tremor information about the hand of the user acquired by the first detection circuit 300, rectilinear movement components of the handle 200 in the X-axis direction, the Y-axis direction and the Z-axis direction in the three-dimensional coordinate system and rotational movement components of the handle 200 in the case that the handle rotates about the at least two coordinate axes in the three-dimensional coordinate system as the central axes, acquire, in accordance with the rectilinear movement components and the rotational movement components, a compensating movement component for cancelling out an influence of the movement of the handle 200 on the movement of the functional body 100, and control the operating state of the movement mechanism 500 in accordance with the compensating movement component.

Based on the above, the functional body 100 may perform translational compensating movement and rotational compensating movement, so as to cancel out the hand tremor in a better manner.

In the case that the handle 200 is held by the user, it may move synchronously with the hand and have six degrees of movement freedom which, as shown in FIG. 1, include translation movement and rotational movement in the X-axis direction, the Y-axis direction and the Z-axis direction in the three-dimensional coordinate system. In FIG. 1, $a_{x0}$ represents a rectilinear movement component of the handle 200 in the X-axis direction, $a_{y0}$ represents a rectilinear movement component of the handle 200 in the Y-axis direction, azo represents a rectilinear movement component of the handle 200 in the Z-axis direction, $\omega_{x0}$ represents a rotational movement component of the handle 200 in the case of rotating about an X-axis as a central axis, $\omega_{y0}$ represents a rotational movement component of the handle 200 in the case of rotating about a Y-axis as a central axis, and $\omega_{z0}$ represents a rotational movement component of the handle 200 in the case of rotating about a Z-axis as a central axis.

The functional body 100 may move along with the movement of the handle 200, so identically the functional body 100 may have six degrees of movement freedom. In FIG. 1, $a_{x1}$ represents a rectilinear movement component of the functional body 100 in the X-axis direction, $a_{y1}$ represents a rectilinear movement component of the functional body 100 in the Y-axis direction, $a_{z1}$ represents a rectilinear movement component of the functional body 100 in the Z-axis direction, $\omega_{x1}$ represents a rotational movement component of the functional body 100 in the case of rotating about the X-axis as a central axis, $\omega_{y1}$ represents a rotational movement component of the functional body 100 in the case of rotating about the Y-axis as a central axis, and $\omega_{z1}$ represents a rotational movement component of the functional body 100 in the case of rotating about the Z-axis as a central axis.

The first detection circuit 300 of the handle 200 may detect a movement state of the handle 200. The control circuit 600 may calculate the tremor components of $a_{x0}$, $a_{y0}$, $a_{z0}$, $\omega_{x0}$, $\omega_{y0}$ and $\omega_{z0}$ of the handle 200 in accordance with the movement state of the handle 200 and the movement state of the functional body 100, calculate an influence of each of the tremor components on the movement of the functional body 100 according to the tremor components, calculate compensating movement components $\Delta a_x$, $\Delta a_y$, $\Delta a_z$, $\Delta \omega_x$, $\Delta \omega_y$ and $\Delta \omega_z$ to be applied to the functional body 100 for cancelling out the influences, and control the movement mechanism 500 in accordance with the compensating movement components, so as to enable the functional body 100 to perform the compensating movement, thereby to stabilize a position of the functional body 100.

It should be appreciated that, $\omega_{y1}$ is acquired by taking the functional body 100 itself as the rotating axis. Taking the cup as an example, the cup body is of a cylindrical shape, so the influence of an angular speed of the cup about the Y-axis as the central axis on the use of the cup is limited, so it is unnecessary to perform the compensating movement in the Y-axis direction.

The handheld device will be described hereinafter in conjunction with the embodiments.

As shown in FIG. 2, in one possible embodiment of the present disclosure, the handle 200 has a main body extending in the Y-axis direction, and a first end and a second end arranged opposite to each other. The first end and the second end of the handle 200 are connected to the functional body 100 through the movable connector 400.

The movement mechanism 500 includes a first movement assembly arranged at the first end of the handle 200 and a second movement assembly arranged at the second end of the handle 200. The first movement assembly includes a first X-axis-direction movement member 511 configured to control the functional body 100 to move rectilinearly relative to the first end of the handle 200 in the X-axis direction, a first Y-axis-direction movement member 512 configured to control the functional body 100 to move rectilinearly relative to the first end of the handle 200 in the Y-axis direction, and a first Z-axis-direction movement member 513 configured to control the functional body 100 to move rectilinearly relative to the first end of the handle 200 in the Z-axis direction. The second movement assembly includes a second X-axis-direction movement member 521 configured to control the functional body 100 to move rectilinearly relative to the second end of the handle 200 in the X-axis direction, a second Y-axis-direction movement member 522 configured to control the functional body 100 to move rectilinearly relative to the second end of the handle 200 in the Y-axis direction, and a second Z-axis-direction movement member 523 configured to control the functional body 100 to move rectilinearly relative to the second end of the handle 200 in the Z-axis direction.

The control circuit 600 is further configured to, in accordance with the compensating movement component: control the first X-axis-direction movement member 511 and the second X-axis-direction movement member 521 to drive the functional body 100 to move relative to the first end and the second end of the handle 200 in the X-axis direction synchronously, thereby to control the functional body 100 to move rectilinearly in the X-axis direction; control the first X-axis-direction movement member 511 and the second X-axis-direction movement member 521 to drive the functional body 100 to move relative to the first end and the second end of the handle 200 in the X-axis direction asynchronously, thereby to control the functional body 100 to rotate about a Z-axis as the central axis; control the first Y-axis-direction movement member 512 and the second Y-axis-direction movement member 522 to drive the functional body 100 to move relative to the first end and the second end of the handle 200 in the Y-axis direction synchronously, thereby to control the functional body 100 to move rectilinearly in the Y-axis direction; control the first Z-axis-direction movement member 513 and the second Z-axis-direction movement member 523 to drive the functional body 100 to move relative to the first end and the second end of the handle 200 in the Z-axis direction synchronously, thereby to control the functional body 100 to move rectilinearly in the Z-axis direction; and control the first Z-axis-direction movement member 513 and the second Z-axis-direction movement member 523 to drive the functional body 100 to move relative to the first end and the second end of the handle 200 in the Z-axis direction asynchronously, thereby to control the functional body 100 to rotate about an X-axis as the central axis.

Based on the above, in this embodiment of the present disclosure, two three-dimensional rectilinear movement assemblies, i.e. the first movement assembly and the second movement assembly are adopted and applied to the connection between the functional body 100 and the handle 200. Through the synchronous and asynchronous movements of these two movement assemblies, it enables the translation movement and rotational movement of the functional body 100 to cancel out the hand tremor.

Figure 3:
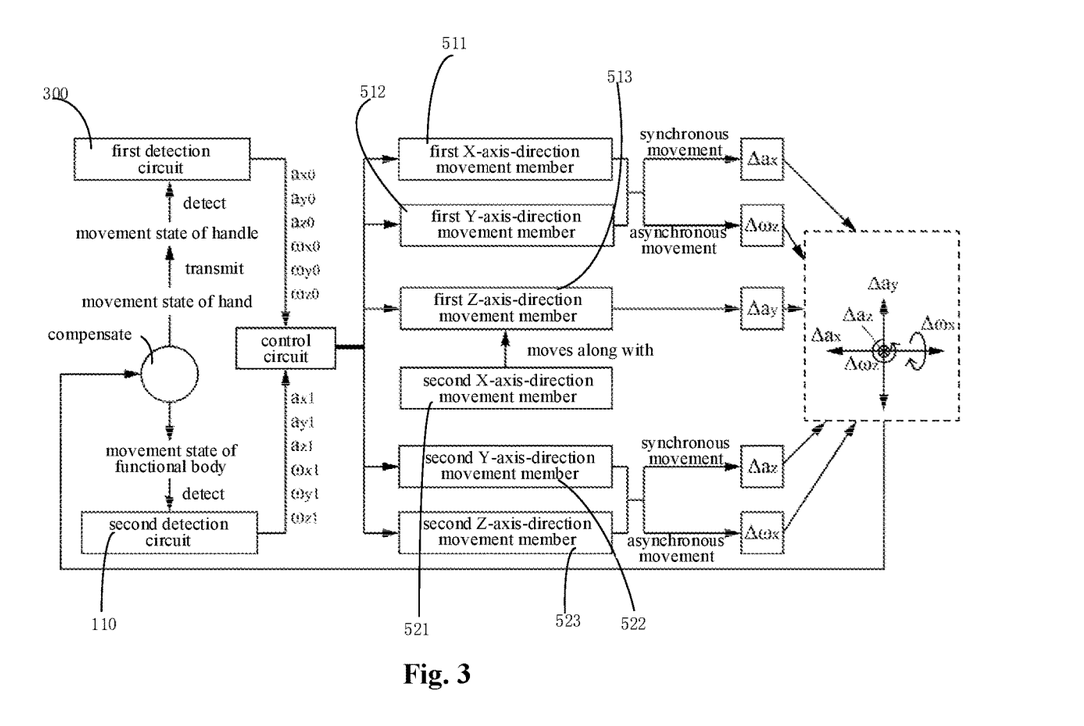
FIG. 3 is a schematic view showing an operating principle of the handheld device in FIG. 2.

To be specific, as shown in FIGS. 2 and 3, a translational acceleration $\Delta a_x$ of the functional body 100 in the X-axis direction may be caused by the synchronous movement of the first X-axis-direction movement member 511 and the second X-axis-direction movement member 521, a rotational angular speed $\Delta \omega_z$ of the functional body 100 about the Z-axis may be caused by the asynchronous movement of the first X-axis-direction movement member 511 and the second X-axis-direction movement member 521, a translational acceleration $\Delta a_y$ of the functional body 100 in the Y-axis direction may be caused by the first Y-axis-direction movement member 512 driving the second Y-axis-direction movement member 522 to move synchronously with the movement of the first Y-axis-direction movement member 512, a translational acceleration $\Delta a_z$ of the functional body 100 in the Z-axis direction may be caused by the synchronous movement of the first Z-axis-direction movement member 513 and the second Z-axis-direction movement member 523, and a rotational angular speed $\Delta \omega_x$ of the functional body 100 about the Z-axis may be caused by the asynchronous movement of the first Z-axis-direction movement member 513 and the second Z-axis-direction movement member 523.

In a possible embodiment of the present disclosure, the functional body 100 is provided with a second detection circuit 110 configured to detect a movement state of the functional body 100. The control circuit 600 is further configured to control the operating state of the movement mechanism 500 in accordance with a signal from the second detection circuit, so as to perform negative feedback correction on the compensating movement of the functional body 100.

Based on the above, it is able to compensate for the tremor through superimposing the compensating movement components $\Delta a_x$, $\Delta a_y$, $\Delta a_z$, $\Delta \omega_x$ and $\Delta \omega_z$ onto the movement of the functional body 100. The movement state of the functional body 100 (i.e., $a_{x1}$, $a_{y1}$, $a_{z1}$, $\omega_{x1}$, $\omega_{y1}$ and $\omega_{z1}$) may be detected by the second detection circuit 110, and then the control circuit 600 may evaluate a compensating effect in accordance with the movement state of the functional body 100 detected by the second detection circuit 110, so as to perform the negative feedback correction on the compensating movement.

In a possible embodiment of the present disclosure, the first detection circuit 300 is a first inertial sensor, and the second detection circuit 110 is a second inertial sensor.

It should be appreciated that, in this embodiment of the present disclosure, the functional body 100 is connected to the handle 200 via the movable connector 400. The movable connector 400 includes a first connector 401 and a second connector 402. The first end of the handle 200 is connected to the functional body 100 via the first connector 401, and the second end of the handle 200 is connected to the functional body 100 via the second connector 402. Each of the movement members of the first movement assembly may be connected to the first connector 401 and has a driving ability to drive the functional body 100 to move rectilinearly relative to the first end of the handle 200 in the X-axis direction, the Y-axis direction and the Z-axis direction. Each of the movement members of the second movement assembly may be connected to the second connector 402, and the second X-axis-direction movement member 521 and the second Z-axis-direction movement member 523 of the movement members of the second movement assembly may have a driving ability to drive the functional body 100 to move rectilinearly relative to the second end of the handle 200 in the X-axis direction and the Z-axis direction. The second Y-axis-direction movement member 522 of the second movement assembly may not have any driving ability. In the case that the functional body 100 is driven by the first Y-axis-direction movement member 512 to move relative to the handle 200 in the Y-axis direction, the second Y-axis-direction movement member 522 may move synchronously in the Y-axis direction.

In addition, in this embodiment of the present disclosure, each of the first X-axis-direction movement member 511, the first Y-axis-direction movement member 512, the first Z-axis-direction movement member 513, the second X-axis-direction movement member 521, the second Y-axis-direction movement member 522 and the second Z-axis-direction movement member 523 is provided with a position sensor configured to detect a position of the respective movement member, so as to acquire a position of the functional body 100 relative to the handle 200. The position sensor may be a Hall magnetic sensor or grating counter, and a structure of the position sensor will not be particularly defined herein.

It should be appreciated that, a driving mechanism of each movement member of each of the first movement assembly and the second movement assembly will not be particularly defined herein, and various driving modes, e.g., a driving motor or a set of gears, may be adopted.

In addition, a connection structure between each movement member of each of the first movement assembly and the second movement assembly and the corresponding one of the first connector 401 and the second connector 402 will not be particularly defined herein, as long as the movement member is capable of driving the functional body 100 to move relative to the handle 200 through the movable connector 400.

In addition, the handheld device is further provided with a power source 800 and a charger 700. The power source 800 is configured to supply power to the first detection circuit 300, the second detection circuit 110, the control circuit 600 and the driving mechanism of each movement member. The charger may be a charging interface arranged on the handheld device, e.g., a wireless charging coil.

As shown in FIG. 4, in another possible embodiment of the present disclosure, the handle 200 is provided with a main body extending in the Y-axis direction, and a first end and a second end arranged opposite to each other. The first end of the handle 200 is connected to the functional body 100 via the movable connector 400, and the second end of the handle 200 is not connected to the functional body 100.

The movement mechanism 500 includes: a third X-axis-direction movement member 531 configured to control the functional body 100 to move rectilinearly relative to the first end of the handle 200 in the X-axis direction; a third Y-axis-direction movement member 532 configured to control the functional body 100 to move rectilinearly relative to the first end of the handle 200 in the Y-axis direction; a third Z-axis-direction movement member 533 configured to control the functional body 100 move rectilinearly relative to the first end of the handle 200 in the Z-axis direction; a first rotation member 534 configured to control the functional body 100 to rotate about an X-axis as the central axis; and a second rotation member 535 configured to control the functional body 100 to rotate about a Z-axis as the central axis.

The control circuit 600 is further configured to control an operating state of each of the third X-axis-direction movement member 531, the third Y-axis-direction movement member 532, the third Z-axis-direction movement member 533, the first rotation member 534 and the second rotation member 535 in accordance with the compensating movement component.

Based on the above, in this embodiment of the present disclosure, a set of three-dimensional rectilinear movement members and a set of rotation members are used so as to drive the functional body 100 to perform the translational compensating movement and the rotational compensating movement, thereby to cancel out the hand tremor.

Figure 5:
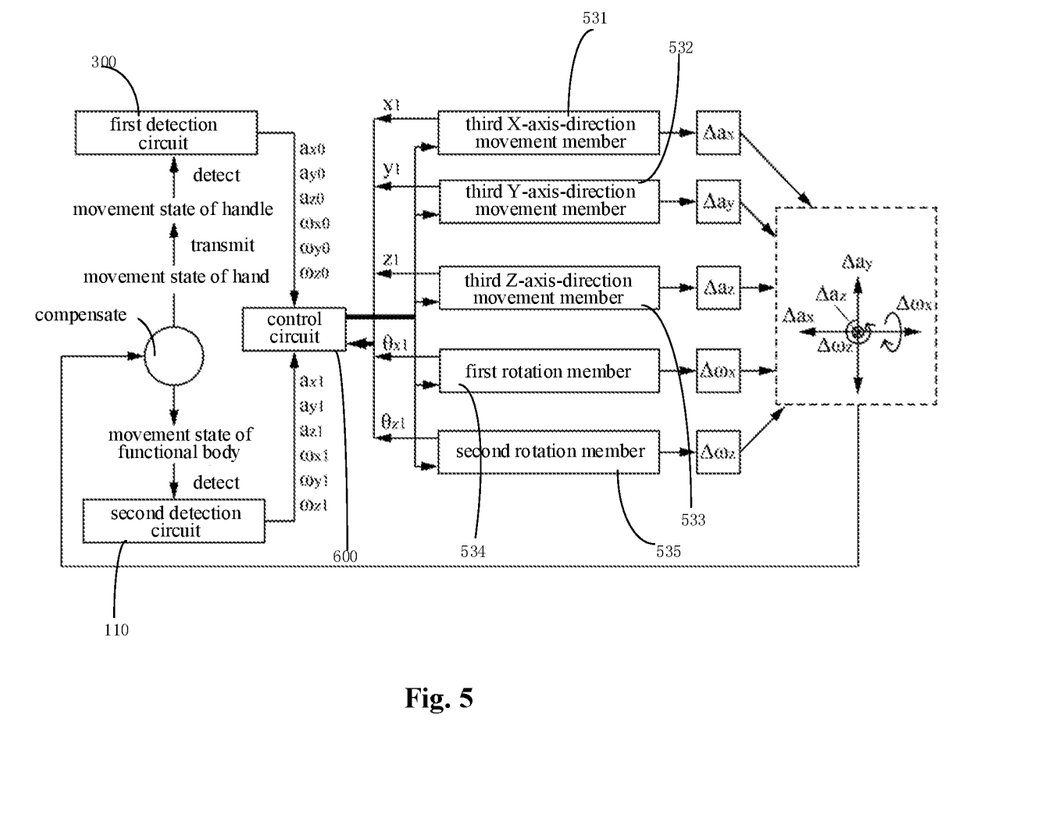
FIG. 5 is a schematic view showing the operating principle of the handheld device in FIG. 4.

To be specific, as shown in FIGS. 4 and 5, a translational acceleration $\Delta a_x$ of the functional body 100 relative to the handle 200 in the X-axis direction may be caused by the third X-axis-direction movement member 531, a translational acceleration $\Delta a_y$ of the functional body 100 relative to the handle 200 in the Y-axis direction may be caused by the third Y-axis-direction movement member 532, a translational acceleration $\Delta a_z$ of the functional body 100 relative to the handle 200 in the Z-axis direction may be caused by the third Z-axis-direction movement member 533, a rotational angular speed $\Delta \omega_x$ of the functional body 100 relative to the handle 200 about the X-axis may be caused by the first rotation member 534, and a rotational angular speed $\Delta \omega_z$ of the functional body 100 relative to the handle 200 about the Z-axis may be caused by the second rotation member 535.

In a possible embodiment of the present disclosure, the functional body 100 is provided with a second detection circuit 110 configured to detect a movement state of the functional body 100. The control circuit 600 is further configured to control the operating state of the movement mechanism 500 in accordance with a signal from the second detection circuit, so as to perform negative feedback correction on the compensating movement of the functional body 100.

Based on the above, it is able to compensate for the tremor through superimposing the compensating movement components $\Delta a_x$, $\Delta a_y$, $\Delta a_z$, $\Delta \omega_x$ and $\Delta \omega_z$ onto the movement of the functional body 100. The movement state of the functional body 100 (i.e., $a_{x1}$, $a_{y1}$, $a_{z1}$, $\omega_{x1}$, $\omega_{y1}$ and $\omega_{z1}$) may be detected by the second detection circuit 110, and then the control circuit 600 may evaluate a compensating effect in accordance with the movement state of the functional body 100 detected by the second detection circuit 110, so as to perform the negative feedback correction on the compensating movement.

In a possible embodiment of the present disclosure, the first detection circuit 300 is a first inertial sensor, and the second detection circuit 110 is a second inertial sensor.

It should be appreciated that, in this embodiment of the present disclosure, the first end of the handle 200 is connected to the functional body 100 through the first connector 401, and the second end of the handle 200 is not connected to the functional body 100. Each of the movement members of the third movement assembly in the X-axis direction, the Y-axis direction and the Z-axis direction may be connected to the movable connector 400 and has a driving ability so as to drive the functional body 100 to move rectilinearly relative to the first end of the handle 200 in the X-axis direction, the Y-axis direction and the Z-axis direction. Each of the first rotation member 534 and the second rotation member 535 has a driving ability, so as to drive the functional body 100 to rotate relative to the first end of the handle 200 about a corresponding one of the X-axis and the Y-axis.

In addition, in this embodiment of the present disclosure, each of the third X-axis-direction movement member 531, the third Y-axis-direction movement member 532 and the third Z-axis-direction movement member 533 is provided with a position sensor, and each of the first rotation member 534 and the second rotation member 535 is provided with an angular sensor. Each of the sensors is configured to detect a position of the corresponding movement member, so as to acquire a position or an angle of the functional body 100 relative to the handle 200. Each of the position sensors and the angular sensors may be a Hall magnetic sensor or grating counter, and a structure thereof will not be particularly defined herein.

It should be appreciated that, a driving mechanism of each movement member of the first, second, and third movement assembly will not be particularly defined herein, and various driving modes, e.g., a driving motor or a set of gears, may be adopted.

In this embodiment of the present disclosure, each of the first rotation member 534 and the second rotation member 535 may be driven by, but not limited to, a driving motor or a set of gears.

In addition, the first rotation member 534 and the second rotation member 535 may be fixedly connected to the functional body 100 and capable of rotating about the movable connector 400, so as to drive the functional body 100 to rotate relative to the handle 200. Each of the first rotation member 534 and the second rotation member 535 may drive the functional body 100 to rotate through a gear or the like.

In addition, the first rotation member 534 and the second rotation member 535 may be arranged within the functional body 100 or the handle 200, or between the functional body 100 and the handle 200.

It should be appreciated that, a connection structures among the movement members, the first rotation member 534, the second rotation member 535, and the movable connector 400 will not be particularly defined herein, as long as each of the movement members is capable of driving the functional body 100 to move rectilinearly relative to the handle 200, the first rotation member 534, the second rotation member 535 drive the functional body 100 to rotate relative to the handle 200, and the movable connector 400 enables the functional body 100 to move rectilinearly and rotate relative to the handle 200.

In addition, the handheld device is further provided with a power source and a charger. The power source is configured to supply power to the first detection circuit 300, the second detection circuit 110, the control circuit 600 and the driving mechanism of each movement member. The charger may be a charging interface arranged on the handheld device, e.g., a wireless charging coil.

The present disclosure further provides in some embodiments a hand tremor compensation method for use in the above-mentioned handheld device, which includes steps of: detecting a movement state of the handle 200 of the handheld device, so as to acquire hand tremor information about a hand of the user; and driving the functional body 100 of the handheld device to perform compensating movement relative to the handle 200 in accordance with the hand tremor information of the user, so as to maintain the functional body 100 at a selected position.

In a possible embodiment of the present disclosure, the step of detecting the movement state of the handle 200 of the handheld device so as to acquire the hand tremor information about the hand of the user includes: acquiring, in accordance with the acquired hand tremor information about the hand of the user, rectilinear movement components of the handle 200 in an X-axis direction, a Y-axis direction and a Z-axis direction in a three-dimensional coordinate system, and rotational movement components of the handle 200 in the case that the handle 200 rotates about at least two coordinate axes in the three-dimensional coordinate system as central axes. The step of driving the functional body 100 of the handheld device to perform the compensating movement relative to the handle 200 in accordance with the hand tremor information about the hand of the user includes: acquiring a compensating movement component for cancelling out an influence of the movement of the handle 200 on the movement of the functional body 100 in accordance with the rectilinear movement components and the rotational movement components, and controlling the compensating movement of the functional body 100 in accordance with the compensating movement component.

In a possible embodiment of the present disclosure, for the handheld device in FIGS. 2-3, the step of controlling the compensating movement of the functional body 100 in accordance with the compensating movement component includes, in accordance with the compensating movement component: driving the functional body 100 to move relative to a first end and a second end of the handle 200 synchronously in the X-axis direction, so as to control the functional body 100 to move rectilinearly in the X-axis direction; driving the functional body 100 to move relative to the first end and the second end of the handle 200 asynchronously in the X-axis direction, so as to control the functional body 100 to rotate about a Z-axis as a central axis; driving the functional body 100 to move relative to the first end and the second end of the handle 200 synchronously in the Y-axis direction, so as to control the functional body 100 to move rectilinearly in the Y-axis direction; driving the functional body 100 to move relative to the first end and the second end of the handle 200 synchronously in the Z-axis direction, so as to control the functional body 100 to move rectilinearly in the Z-axis direction; and driving the functional body 100 to move relative to the first end and the second end of the handle 200 asynchronously in the Z-axis direction, so as to control the functional body 100 to rotate about an X-axis as a central axis.

In a possible embodiment of the present disclosure, for the handheld device in FIGS. 4-5, the step of controlling the compensating movement of the functional body 100 in accordance with the compensating movement component includes, in accordance with the compensating movement component, controlling an operating state of each of the third X-axis-direction movement member 531, the third Y-axis-direction movement member 532, the third Z-axis-direction movement member 533, the first rotation member 534 and the second rotation member 535, so as to control the functional body 100 to move rectilinearly in the X-axis direction, the Y-axis direction and the Z-axis direction, and control the functional body 100 to rotate about a Z-axis and an X-axis as central axes.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A handheld device, comprising:
a functional body to be used by a user;
one continuous handle capable of being held by the user and provided with a first detection circuit, wherein the first detection circuit is configured to detect a movement state of the handle, to acquire hand tremor information about a hand of the user holding the handle;
a connector connected to the handle;
a movement mechanism connected to the functional body and the connector, and configured to drive the functional body to move relative to the handle; and
a control circuit configured to control an operating state of the movement mechanism in accordance with the hand tremor information about the hand of the user acquired by the first detection circuit, to drive the functional body to perform compensating movement relative to the handle, thereby to maintain the functional body at a selected position, the hand tremor information comprises:
rectilinear movement information about the hand of the user in an X-axis direction, a Y-axis direction and a Z-axis direction in a three-dimensional coordinate system; and
rotational angle information about the hand of the user acquired in the case that the hand of the user rotates about at least two coordinate axes in the three-dimensional coordinate system as central axes;
the movement mechanism is at least capable of driving the functional body to move rectilinearly relative to the handle in the X-axis direction, the Y-axis direction and the Z-axis direction in the three-dimensional coordinate system, and controlling the functional body to rotate relative to the handle about the at least two coordinate axes in the three-dimensional coordinate system as the central axes; and
the control circuit is further configured to:
acquire, in accordance with the hand tremor information about the hand of the user acquired by the first detection circuit, rectilinear movement components of the handle in the X-axis direction, the Y-axis direction and the Z-axis direction in the three-dimensional coordinate system, and rotational movement components of the handle in the case that the handle rotates about the at least two coordinate axes in the three-dimensional coordinate system as the central axes; and
acquire, in accordance with the rectilinear movement components and the rotational movement components, a compensating movement component for cancelling out an influence of the movement of the handle on the movement of the functional body; and
control the operating state of the movement mechanism in accordance with the compensating movement component,
wherein the handle comprises:
a main body extending along the Y-axis direction; and
a first end and a second end arranged opposite to each other, wherein the first end and the second end of the handle are connected to the functional body through a first connector and a second connector respectively,
wherein the movement mechanism comprises:
a first X-axis-direction movement member configured to control the functional body to move rectilinearly relative to the first end of the handle in the X-axis direction, a first Y-axis-direction movement member configured to control the functional body to move rectilinearly relative to the first end of the handle in the Y-axis direction, and a first Z-axis-direction movement member configured to control the functional body to move rectilinearly relative to the first end of the handle in the Z-axis direction; and
a second X-axis-direction movement member configured to control the functional body to move rectilinearly relative to the second end of the handle in the X-axis direction, a second Y-axis-direction movement member configured to control the functional body to move rectilinearly relative to the second end of the handle in the Y-axis direction, and a second Z-axis-direction movement member configured to control the functional body to move rectilinearly relative to the second end of the handle in the Z-axis direction,
wherein the first X-axis-direction movement member, the first Y-axis-direction movement member and the first Z-axis-direction movement member are arranged at the first end of the handle, and the second X-axis-direction movement member, the second Y-axis-direction movement member and the second Z-axis-direction movement member are arranged at the second end of the handle, wherein the control circuit is further configured to, in accordance with the compensating movement component:

control the first X-axis-direction movement member and the second X-axis-direction movement member to drive the functional body to move relative to the first end and the second end of the handle in the X-axis direction asynchronously, to control the functional body to rotate about a Z-axis in the three-dimensional coordinate system as the central axis;

control the first Z-axis-direction movement member and the second Z-axis-direction movement member to drive the functional body to move relative to the first end and the second end of the handle in the Z-axis direction asynchronously, to control the functional body to rotate about an X-axis in the three-dimensional coordinate system as the central axis, wherein the second Y-axis-direction movement member is configured to drive the functional body to move relative to the second end of the handle in the Y-axis direction asynchronously with a movement of the functional body relative to the first end of the handle in the Y-axis direction driven by the first Y-axis-direction movement member.

2. The handheld device according to claim 1, wherein the control circuit is further configured to, in accordance with the compensating movement component:

control the first X-axis-direction movement member and the second X-axis-direction movement member to drive the functional body to move relative to the first end and the second end of the handle in the X-axis direction synchronously, to control the functional body to move rectilinearly in the X-axis direction;

control the first Y-axis-direction movement member and the second Y-axis-direction movement member to drive the functional body to move relative to the first end and the second end of the handle in the Y-axis direction synchronously, to control the functional body to move rectilinearly in the Y-axis direction;

control the first Z-axis-direction movement member and the second Z-axis-direction movement member to drive the functional body to move relative to the first end and the second end of the handle in the Z-axis direction synchronously, to control the functional body to move rectilinearly in the Z-axis direction.

3. The handheld device according to claim 1, wherein the functional body is provided with a second detection circuit configured to detect a movement state of the functional body; and the control circuit is further configured to control the operating state of the movement mechanism in accordance with a signal outputted from the second detection circuit, to perform negative feedback correction on the compensating movement of the functional body.

4. The handheld device according to claim 1, wherein the functional body is further provided with a power source and a charger.

5. The handheld device according to claim 1, wherein the handheld device comprises a cup, wherein the functional body is a main body of the cup, and the handle is a handle of the cup.

6. A hand tremor compensation method applied to the handheld device according to claim 1, comprising:

detecting the movement state of the handle of the handheld device, to acquire the hand tremor information about the hand of the user; and driving the functional body of the handheld device to perform compensating movement relative to the handle in accordance with the hand tremor information, to maintain the functional body at the selected position.

7. The hand tremor compensation method according to claim 6, wherein the step of detecting the movement state of the handle of the handheld device to acquire the hand tremor information about the hand of the user comprises:

acquiring, in accordance with the acquired hand tremor information about the hand of the user, rectilinear movement components of the handle in an X-axis direction, a Y-axis direction and a Z-axis direction in a three-dimensional coordinate system, and rotational movement components of the handle in the case that the handle rotates about at least two coordinate axes in the three-dimensional coordinate system as central axes.

8. The hand tremor compensation method according to claim 7, wherein the step of driving the functional body of the handheld device to perform the compensating movement relative to the handle in accordance with the hand tremor information about the hand of the user comprises:

acquiring a compensating movement component for cancelling out an influence of the movement of the handle on the movement of the functional body in accordance with the rectilinear movement components and the rotational movement components; and controlling the compensating movement of the functional body in accordance with the compensating movement component.

9. The hand tremor compensation method according to claim 8, wherein the step of controlling the compensating movement of the functional body comprises, in accordance with the compensating movement component:

controlling a first X-axis-direction movement member and a second X-axis-direction movement member of the movement mechanism to drive the functional body to move relative to a first end and a second end of the handle synchronously in the X-axis direction, to control the functional body to move rectilinearly in the X-axis direction;

controlling the first X-axis-direction movement member and the second X-axis-direction movement member to drive the functional body to move relative to the first end and the second end of the handle asynchronously in the X-axis direction, to control the functional body to rotate about a Z-axis in the three-dimensional coordinate system as a central axis;

controlling a first Y-axis-direction movement member and a second Y-axis-direction movement member of the movement mechanism to drive the functional body to move relative to the first end and the second end of the handle synchronously in the Y-axis direction, to control the functional body to move rectilinearly in the Y-axis direction;

controlling a first Z-axis-direction movement member and a second Z-axis-direction movement member of the movement mechanism to drive the functional body to move relative to the first end and the second end of the handle synchronously in the Z-axis direction, to control the functional body to move rectilinearly in the Z-axis direction; and controlling the first Z-axis-direction movement member and the second Z-axis-direction movement member to drive the functional body to move relative to the first end and the second end of the handle asynchronously in the Z-axis direction, to control the functional body to rotate about an X-axis in the three-dimensional coordinate system as a central axis.

* * * * *